United States Patent
Tomer et al.

(10) Patent No.: US 12,020,809 B2
(45) Date of Patent: Jun. 25, 2024

(54) SYSTEMS AND METHODS FOR COMPUTER MODELING FOR HEALTHCARE BOTTLENECK PREDICTION AND MITIGATION

(71) Applicant: TeleTracking Technologies, Inc., Pittsburgh, PA (US)

(72) Inventors: Anjali Tomer, Pittsburgh, PA (US); Scott Jubeck, Pittsburgh, PA (US); Ratna Divya Kanthi Bejjam, Bridgeville, PA (US)

(73) Assignee: TELETRACKING TECHNOLOGIES, INC., Pittsburgh, PA (US)

( * ) Notice: Subject to any disclaimer, the term of this patent is extended or adjusted under 35 U.S.C. 154(b) by 131 days.

(21) Appl. No.: 17/769,252

(22) PCT Filed: Oct. 18, 2020

(86) PCT No.: PCT/US2020/056211
§ 371 (c)(1),
(2) Date: Apr. 14, 2022

(87) PCT Pub. No.: WO2021/077059
PCT Pub. Date: Apr. 22, 2021

(65) Prior Publication Data
US 2023/0317256 A1    Oct. 5, 2023

Related U.S. Application Data

(60) Provisional application No. 62/923,119, filed on Oct. 18, 2019.

(51) Int. Cl.
*G16H 40/20* (2018.01)
*G06Q 10/0631* (2023.01)
*G06Q 10/067* (2023.01)

(52) U.S. Cl.
CPC ....... *G16H 40/20* (2018.01); *G06Q 10/06311* (2013.01); *G06Q 10/067* (2013.01)

(58) Field of Classification Search
CPC . G16H 40/20; G06Q 10/06311; G06Q 10/067
See application file for complete search history.

(56) References Cited

U.S. PATENT DOCUMENTS

| | | | |
|---|---|---|---|
| 7,698,055 B2 * | 4/2010 | Horvitz | G08G 1/0104 342/357.31 |
| 8,799,009 B2 * | 8/2014 | Mellin | G06Q 10/0639 709/204 |

(Continued)

FOREIGN PATENT DOCUMENTS

| | | | | |
|---|---|---|---|---|
| CN | 107742168 A | * | 2/2018 | ............. G06Q 10/04 |
| CN | 110163436 A | * | 8/2019 | ............. G06Q 10/04 |
| WO | 2014062644 A1 | | 4/2014 | |

OTHER PUBLICATIONS

Wald et al., "Personalized Health Care and Health Information Technology Policy: An Exploratory Analysis", Brigham and Women's Hospital, Harvard Medical School, Boston, MA, USA. MedInfo 2013. (Year: 2013).*

(Continued)

*Primary Examiner* — Pan G Choy
(74) *Attorney, Agent, or Firm* — FERENCE & ASSOCIATES LLC

(57) ABSTRACT

Systems and methods are disclosed for managing predictive bottleneck models. The system receives, from a user device, bottleneck data indicating a bottleneck within a facility. The system compiles, based on the received indication, contextual data associated with the bottleneck. The system analyzes the bottleneck data and the contextual data conjunctively and determines a relationship between the bottleneck (Continued)

data and the contextual data. The system updates a predictive bottleneck model based on the determined relationship.

20 Claims, 10 Drawing Sheets

(56) References Cited

U.S. PATENT DOCUMENTS

| | | | |
|---|---|---|---|
| 2002/0107769 A1* | 8/2002 | Dashefsky | G06Q 40/03 705/35 |
| 2002/0143497 A1* | 10/2002 | Roser | G05B 15/02 702/182 |
| 2011/0128920 A1* | 6/2011 | Lee | H04W 72/541 370/329 |
| 2014/0108034 A1 | 4/2014 | Akbay et al. | |
| 2015/0310739 A1* | 10/2015 | Beaurepaire | G08G 1/096716 701/117 |
| 2017/0193168 A1* | 7/2017 | Wood | A61K 35/17 |
| 2017/0303187 A1* | 10/2017 | Crouthamel | G06K 7/10297 |
| 2018/0107797 A1* | 4/2018 | Schuck et al. | G06F 17/30 |
| 2019/0279135 A1 | 9/2019 | Wilkerson et al. | |

OTHER PUBLICATIONS

Ilarri et al., "A Review of the Role of Sensors in Mobile Context-Aware Recommendation Systems", IIS Department, University of Zaragoza, 50018 Zaragoza, Spain. Hindawi Publishing Corporation, International Journal of Distributed Sensor Networks, vol. 2015, Article Id 489264, 30 pages. (Year: 2015).*

Cheng et al., "Mobile Big Data: The Fuel for Data-Driven Wireless", IEEE Internet of Things Journal, vol. 4, No. 5, Oct. 2017. (Year: 2017).*

International Search Report and Written Opinion for PCT/US2020/056211, Feb. 1, 2021, 3 pages.

European Patent Office, Supplementary European Search Report from Application No. EP20877301, Oct. 6, 2023, 5 pages.

* cited by examiner

SYSTEMS AND METHODS FOR COMPUTER MODELING FOR HEALTHCARE BOTTLENECK PREDICTION AND MITIGATION

BACKGROUND

Modern health care facilities have highly skilled personnel, high-tech patient monitoring systems, employee communication systems, and in some instances, patient and equipment location tracking systems. High efficiency, however, still evades many modern facilities, and many hospitals still fail to deliver the best possible health care to their patients, and fail to operate at maximum possible capacity. There are multiple underlying reasons for inefficiencies. As one example, health care facilities and organizations often have segregated departments and units, causing organizational barriers to providing the best care, especially when the departments and units do not coordinate schedules and their respective roles in caring for a patient. Various pieces of patient data, such as patient flow data, may be segregated across different locations, making it difficult to manage treatment across an entire facility.

In many cases, facilities may suffer from various bottlenecks to patient care, which may be caused by caregivers or other staff, such when caregivers bring too many patients to a given location at the same time. In addition, a lack of integration and comprehensive data analysis in traditional systems prevents healthcare systems from operating at the potential capacity. Traditional systems also fail to consider many data points that are observable using the proper equipment. Bottlenecks and/or unforeseen surges in workflow can also increase stress on caregivers, further decreasing the quality of care to patients.

In view of the problems facing hospitals and other health care facilities, improved systems and methods for managing patient care bottlenecks are needed.

SUMMARY

Disclosed embodiments relate to computerized systems and methods for creating and updating predictive bottleneck models, and bottleneck mitigation.

Systems and methods are disclosed for configuring predictive bottleneck models, which may predict a possible future bottleneck at a facility or enterprise. Disclosed embodiments also replace subjective analyses of traditional techniques with automatic analyses, which may be rule based, of the aggregated data related to bottlenecks and other contextual sources, using particular rules and mechanisms disclosed herein. Some embodiments of disclosed systems also use arrangements of sensors across one or more facilities in combination with particular database structures to allow for such aggregation and analysis automation and to integrate new types of data into predictive models that could not be collected and analyzed using traditional techniques. Based on the analyses, models for predicting a bottleneck within a facility or enterprise may be modified to better predict future bottlenecks.

In addition, the provided systems and methods may predict a future bottleneck and generate interactive graphical user interfaces (GUIs) having recommendations based on an analysis of aggregated data and application of a model that determines recommended corrective actions based on real time environment conditions. Some embodiments of the disclosed system further apply one or more rule sets to determine corrective actions based on how such actions may influence other potential bottlenecks. Accordingly, the disclosed embodiments may improve users' experiences with healthcare metric systems, may improve prediction of bottlenecks, may improve the responsiveness to bottlenecks and eliminate inefficiencies, and may increase the efficiency of healthcare systems to allow existing resources to serve more patients. Any or all of these improvements can increase the quality of patient care.

Consistent with the present embodiments, a computerized system for managing predictive bottleneck models is disclosed. The system may comprise at least one processor in communication with a communications network; and a storage medium comprising instructions that, when executed, may configure the at least one processor to receive, from a user device, bottleneck data indicating a bottleneck within a facility; compile, based on the received indication, contextual data associated with the bottleneck; analyze the bottleneck data and the contextual data conjunctively; determine a relationship between the bottleneck data and the contextual data; and update a predictive bottleneck model based on the determined relationship.

Consistent with the present embodiments, one or more computerized methods are disclosed, corresponding to the exemplary system disclosed above.

Consistent with other disclosed embodiments, non-transitory computer readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and, together with the description, serve to explain the disclosed principles. In the drawings.

DETAILED DESCRIPTION OF EXEMPLARY EMBODIMENTS

Reference will now be made in detail to exemplary embodiments, examples of which are illustrated in the accompanying drawing and disclosed herein. Wherever convenient, the same reference numbers will be used throughout the drawings to refer to the same or like parts.

Figure 1:
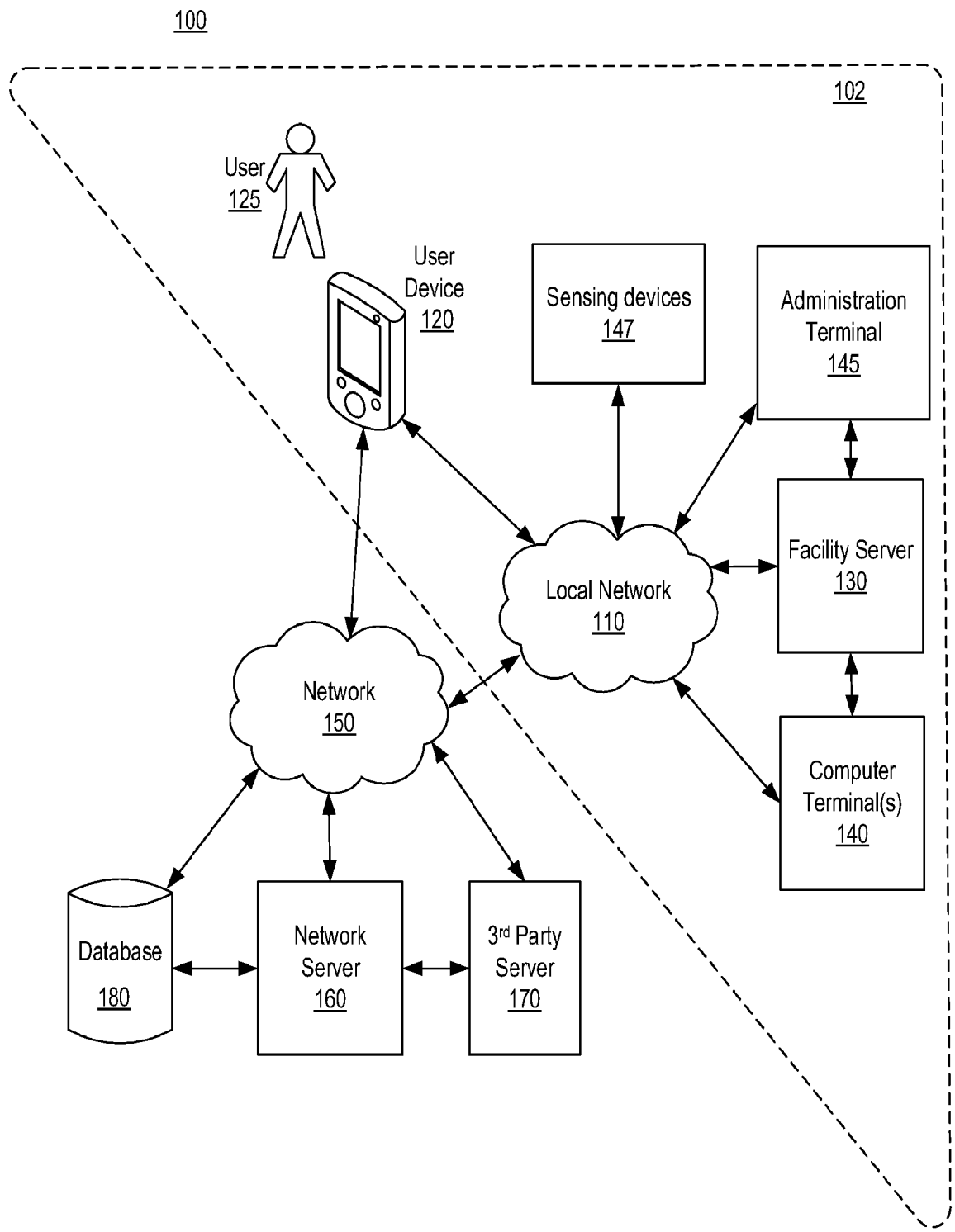
FIG. 1 depicts an example of a system environment for responding to bottlenecks within an organization, consistent with embodiments of the present disclosure.

FIG. 1 shows a diagram of a computer system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, system 100 may include a facility server 130, a computer terminal 140, an administration terminal 145, a user device 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and user device 120 may be physically disposed within a facility such as a medical facility such as a hospital or office building (i.e. as facility system 102) while network 150, network server 160, third party server 170, and database 180 may be external to the medical facility. Other components known to one of ordinary skill in the art may be included in system 100 to perform tasks consistent with the disclosed embodiments. For example, in some embodiments, facility system 102 may include one or more sensor devices such as sensing devices 147 located throughout the facility to monitor one or more conditions such as occupancy, temperature, humidity, proximity, movement, and other parameters indicative of a status or condition of a room, area, equipment, or supplies. In some embodiments, sensing devices 147 may be disposed throughout one or more areas of a hospital as part of a security system or a real-time locating system. Sensing devices 147 may be any number of infrared sensors, motion sensors, piezoelectric sensors, laser sensors, sonar sensors, GPS sensors, electromagnetic sensors, and the like. In some embodiments, a sensing device 147 may be a virtual sensor running within software (e.g., that detects particular computing activity, such as CPU usage, a process running, etc.), which may operate within a computing device of system 100 and/or system 700 (e.g. user device 120). Additionally, in some embodiments facility system 102 may include one or more wireless receivers (not shown) configured to detect one or more wireless sensor or locating tags, to track a location of a tagged item and/or person, or a condition about the tagged item and/or person.

Computer terminal 140 may be a standalone device disposed in an office, a room, an employee station, or an alternative central location in a workplace. In some embodiments, computer terminal 140 may be a desktop or notebook computer, a flat panel or projected display, touch screen monitor, or any other display. In some embodiments, computer terminal 140 may be associated with a particular room in a facility, such as a particular patient room, hotel room, conference room, or any other type of room. Thus, a message, task request, or other data communication received from a computer terminal 140 may automatically associate the task request, message, or other data communication with the room in which computer terminal 140 is installed.

Administrator terminal 145 may include a computer system or device associated with a user 125 that manages or oversees a portion of facility system 102. For example, administrator terminal 145 may comprise a computer system located at a head nurse station, a housekeeping manager's office, a project manager's office, or any other department manager's office or station.

User 125 may be an employee in a workplace environment such as a factory floor worker, delivery transporter, physician, nurse, a technician, supervisor, manager, support personnel, dispatcher, or any individual involved with the care of a patient. In some embodiments, user 125 may be a patient in a hospital (e.g., providing information regarding location, symptoms, ratings for satisfaction of care, indication of delay, and any other information relevant to a patient diagnosis, or treatment protocol and itinerary). In other embodiments, user 125 may be a customer of a business. User 125 may operate computer terminal 140, user device 120, and/or another computer (not shown) to interact with system 100. System 100 may include multiple types of users such as, for example, caregivers, technicians, task requestors, dispatchers, and responders. Task requestors may include one or more individuals who initiate a request for a certain task to be completed, such as a nurse requesting a hospital bed. In some embodiments, dispatchers may include individuals who perform one or more tasks related to assigning requested tasks. In some embodiments, responders may include one or more individuals assigned to the requested tasks, who perform and complete the tasks. In some embodiments, a supervisor or a manager may oversee task throughput and may task an action (e.g. approve a recommended bottleneck fix) to direct workflow.

User device 120 may be a personal computing device such as, for example, a general purpose or notebook computer, a mobile device with computing ability such as a tablet, smartphone, wearable device such as Google Glass™ or smart watches, or any combination of these computers and/or affiliated components. In some embodiments, user device 120 may be a computer system or mobile computer device that is operated by user 125. In some embodiments, user device 120 may be associated with a particular individual such as user 125, such that task assignments directed toward user 125 are sent to mobile device 120.

In some embodiments, user device 120 may communicate with facility server 130 and/or network server 160 via direct wireless communication links (not shown), or via a combination of one or more of local network 110 and/or network 150.

Facility server 130 may be operated by a facility such as a hospital, factory, production facility, port, public transportation facility, business, retail location, and the like. Facility server 130 may enable communication within a computer-based system including computer system components such as desktop computers, workstations, tablets, handheld computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™, Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection. In some embodiments, local network 110 may comprise a portion of network 150 or an extension of network 150.

Network server 160, third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Service™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service, Azure Mobile Services, or Google Cloud Messaging. In such embodiments, third party server 170 may handle the delivery of messages and notifications related to functions of the disclosed embodiments, such as task creation, task assignment, task alerts, and task completion messages and notifications. In some embodiments, network server 160, third party server 170, and/or database 180 may be a single server, special purpose computer, supercomputer, or other computing device. In some embodiments, network server 160, third party server 170, and/or database 180 may perform operations related to maintaining, updating, configuring, and otherwise managing models related to bottleneck management, consistent with the disclosed embodiments.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and message-related functions of the disclosed embodiments. In some embodiments, there may be multiple network servers 160, $3^{rd}$ party servers 170, and/or databases 180, which may operate as part of a computer cluster, which may be cloud-based.

Figure 2:
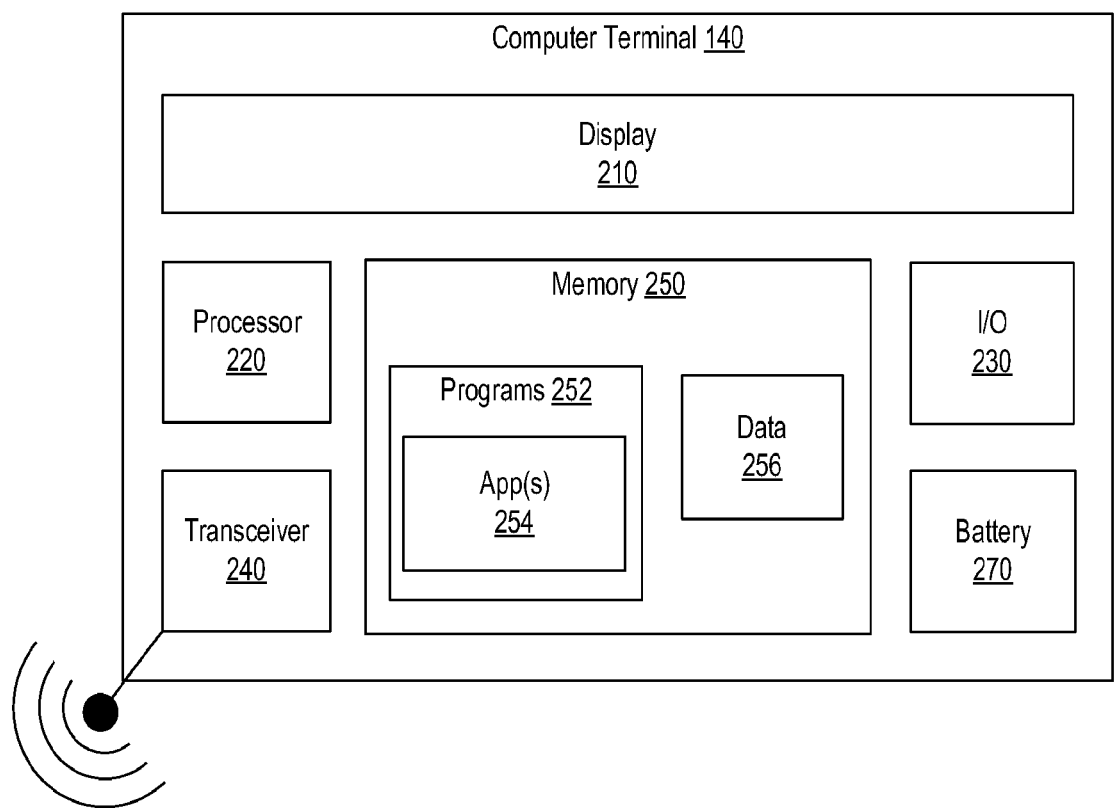
FIG. 2 depicts an example of a computer terminal, consistent with embodiments of the present disclosure.

FIG. 2 shows a diagram of computer terminal 140, consistent with disclosed embodiments. As shown, computer terminal 140 may include a display 210, one or more processors 220, input/output ("I/O") devices 230, a transceiver 240, and memory 250.

Display 210 may include one or more screens for displaying task management information such as, for example, liquid crystal display (LCD), plasma, cathode ray tube (CRT), or projected screens.

Processor 220 may be one or more known processing devices, such as microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. For example, processor 220 may spin up any number of virtual computing instances in order to perform a particular task, which may be based upon the complexity of the task and may be spun down following completion of the task. In another embodiment, processor 220 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from a user. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 140 and other devices of system 100 via, for example, local network 110 and/or network 150. For example, transceiver 240 may include circuitry and one or more antennas for communicating wirelessly with local network 110 using a short range/near-field wireless communication protocol such as Bluetooth™ Bluetooth™ LE, WiFi, and Zigbee. Further, transceiver 240 may communicate with network 150 and/or local network 110 using any known network protocol including any form of wired or wireless internet access.

Memory 250 may include a volatile or non-volatile, magnetic, semiconductor, solid-state, tape, optical, removable, non-removable, or other type of storage device or tangible (i.e., non-transitory) computer-readable medium that stores one or more program(s) 252, such as app(s) 254, and data 256. Data 256 may include, for example, user information, task information, and display settings and preferences. In some embodiments, data 256 may include one or more rule sets for detecting and responding to bottlenecks.

Program(s) 252 may include operating systems (not shown) that perform known operating system functions when executed by one or more processors. By way of example, the operating systems may include Microsoft Windows™, Unix™, Linux™, Android™ and Apple™ operating systems, Personal Digital Assistant (PDA) type operating systems, such as Microsoft CE™, or other types of operating systems. Accordingly, disclosed embodiments may operate and function with computer systems running any type of operating system. Computer terminal 140 may also include communication software that, when executed by a processor, provides communications with network 150 and/or local network 110, such as Web browser software, tablet, or smart handheld device networking software, etc.

Program(s) 252 may also include app(s) 254, such as a bottleneck detection and response app, which when executed causes computer terminal 140 to perform processes related to providing notifications related to a detected bottleneck, altering models related to bottleneck management, and performing a corrective action to mitigate a bottleneck. For example, app(s) 254 may configure computer terminal 140 to generate and display one or more dynamic patient care throughput display and control interfaces, to provide a calculated patient care throughput statistics for a facility or enterprise, display a real-time status of patients progress through itineraries or other metrics, identify potential bottlenecks or complications in patient care, and provide one or more alternative fixes to mitigate the delays or complications, receive instructions from one or more user 125. Furthermore, app(s) 254 may perform one or more automated tasks associated with the patient itinerary including, for example, generating one or more job tasks related to the patient itinerary based on the patient's status and progress, canceling and/or rescheduling one or more job tasks based on changes in the itinerary, requesting equipment or supplies associated with a task, and tracking the real-time status of all tasks related to the patient itinerary. In some embodiments, app(s) 254 may configure one or more computer systems to analyze historical patient care throughput data and hospital performance data to identify patterns, trends or correlative relationships in the historical data. For example, trends in historical data may indicate that certain patient diagnoses are associated with certain lengths of stay, or often experience delays and complications in certain portions of the itinerary. Historical data, identified trends and patterns, and correlative relationships may be identified through regression analysis, queuing analysis and other known statistical analysis methods, stored, and recalled during the creation and/or modification of bottleneck management models, to provide ever-improving patient care and efficiency. Correlations could be stored, retrieved and processed as Stochastic Information Packets (SIPs), Distribution Strings (DIST) or Stochastic Library Unit with Relationships Preserved (SLURPs). As discussed in further detail below, in some embodiments the implementation of these functions and the advantages realized by the present embodiments are attributed to the use of high-speed data and communication network, as well as personal communication and tracking devices disposed throughout a hospital.

Figure 3:
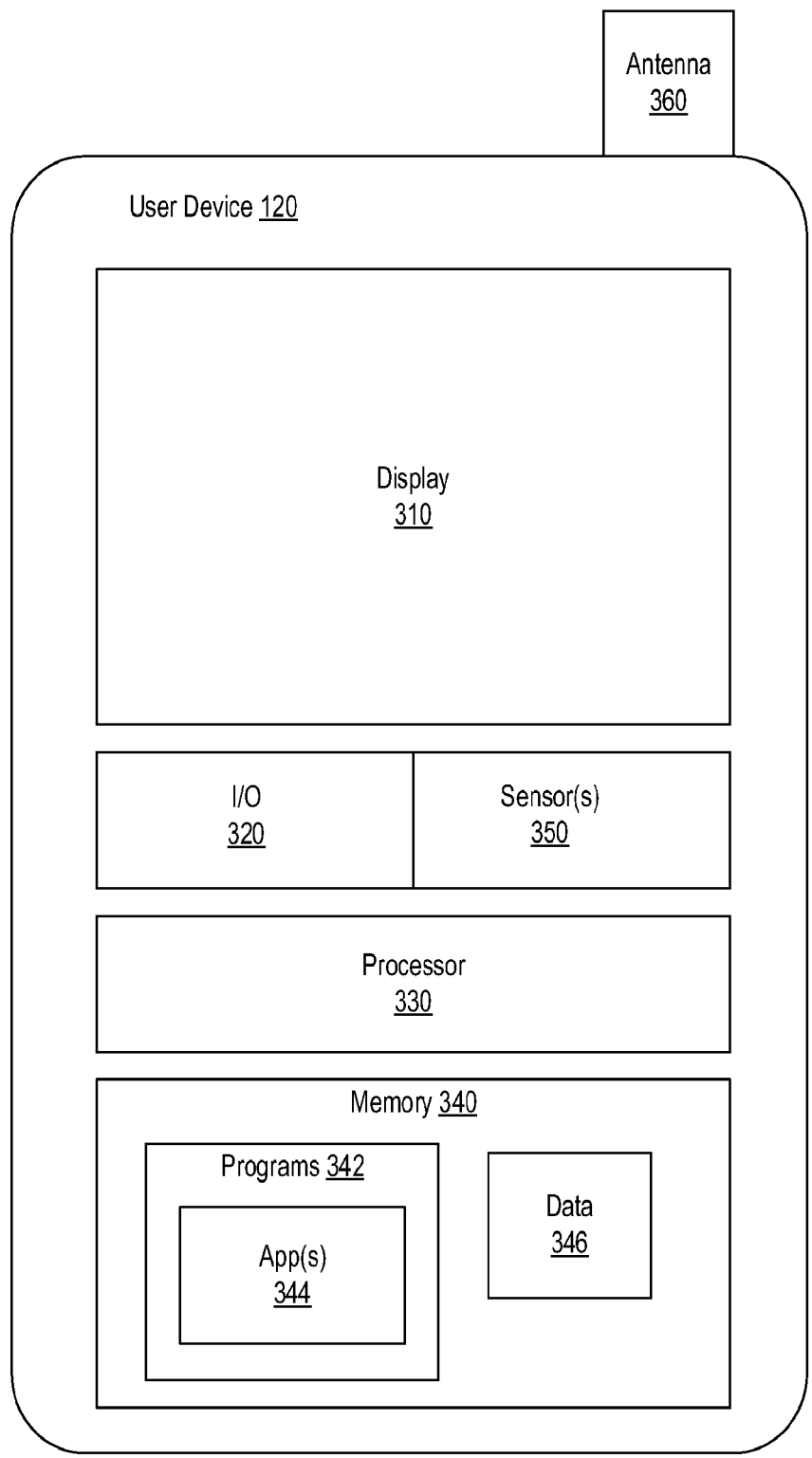
FIG. 3 depicts an example of a user device, consistent with embodiments of the present disclosure.

FIG. 3 shows a diagram of an exemplary user device 120, consistent with disclosed embodiments. As shown, user device 120 may include display 310, I/O device(s) 320, processor 330, memory 340 having stored thereon data 346 and one or more programs 342, such as app(s) 344, sensor(s) 350, and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow mobile device 120 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between mobile device 120 to local network 110, network 150, or by establishing direct wired or wireless connections between user device 120 and other components of system 100. Direct connections may include, for example, Bluetooth™, Bluetooth LE™, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

In some embodiments, user device 120 may contain one or more sensors 350 for collecting environmental, movement, and/or security data. Sensors 350 may include: one or more environmental sensors such as, for example, ambient light sensors, microphones, air pressure sensors, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 330 may use data collected by sensors 350 to control or modify functions of program(s) 342. For example, sensors 350 may track the movement of patients to and from different areas in a hospital (e.g., to identify bottlenecks).

Figure 4:
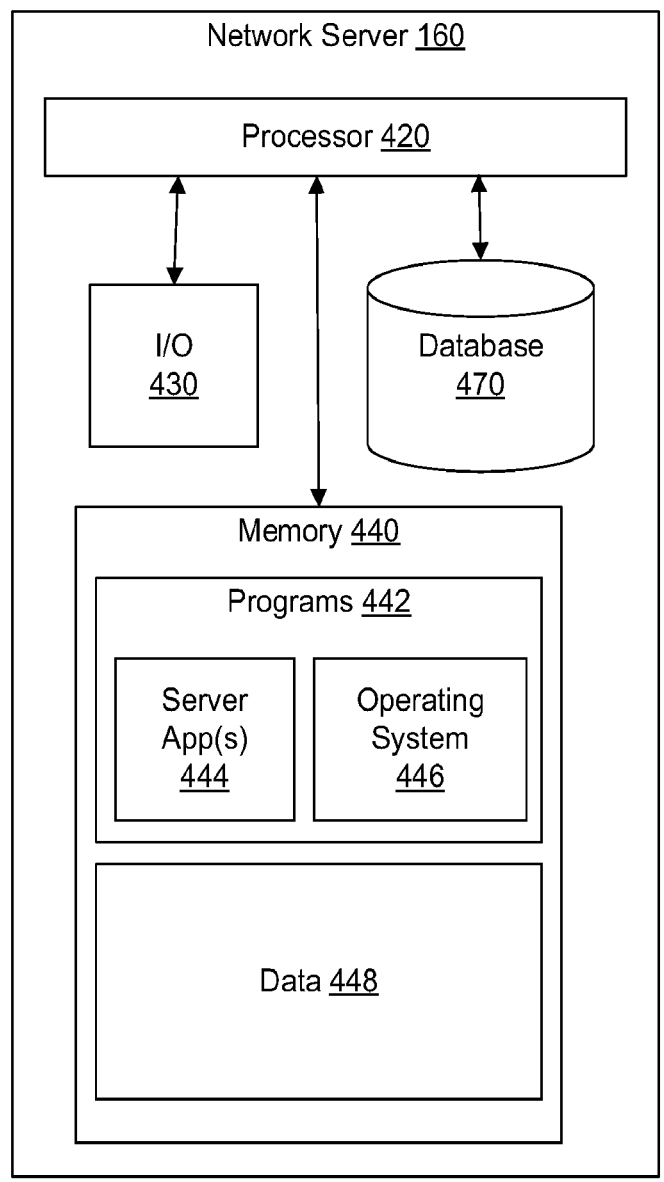
FIG. 4 depicts an example of a network server, consistent with embodiments of the present disclosure.

FIG. 4 shows a diagram of an exemplary network server 160, consistent with disclosed embodiments. In some embodiments, network server 160 may support or provide a cloud computing service, such as Microsoft Azure™ or Amazon Web Services™. In such embodiments, network server 160 may include one or more distributed computer systems (e.g., a computer cluster) capable of performing distributed computing functions and providing cloud computing services and functions consistent with disclosed embodiments. In some embodiments, network server 160 may operate in conjunction with facility server 130. In other embodiments, network server 160 may operate alone, and facility server 130 may be replaced by a network connection to network 150 and/or local network 110. In such embodiments, network server 160 may perform all functions associated with the disclosed methods. In other embodiments, facility server 130 may operate alone, without network server 160. In such embodiments, facility system 102 may operate as a standalone system, in which facility server 130 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

In some embodiments, network server 160 may connect to multiple facilities located in different geographical locations. In such embodiments, network server 160 may manage tasks that span across multiple facilities, such as a request for an equipment item to be transported between facilities. Additionally, network server 160 may collect data from multiple facilities to evaluate performance times in different facilities, and improve the accuracy of expected completion times for different types of tasks using one or more statistical/data regression algorithms.

As shown in FIG. 4, network server 160 may include one or more processor(s) 420, input/output ("I/O") devices 430, memory 440 storing programs 442 (including, for example, server app(s) 444 and operating system 446) and data 448 (including employee data 449), and a database 470. Network server 160 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, network server 160 may also include one or more I/O devices 430 including interfaces for receiving signals or input from devices and providing signals or output to one or more devices that allow data to be received and/or transmitted by network server 160. For example, network server 160 may include interface components, which may provide interfaces to one or more input devices, such as one or more keyboards, mouse devices, and the like, that enable network server 160 to receive input from one or more user 125 that is associated with facility system 102.

In some embodiments, network server 160 may include one or more storage devices configured to store information used by processor 420 (or other components) to perform certain functions related to the disclosed embodiments. In one example, network server 160 may include memory 440 that includes instructions to enable processor 420 to execute one or more applications, such as server applications, an electronic transaction application, an account status application, network communication processes, and any other type of application or software known to be available on computer systems. Alternatively or additionally, the instructions, application programs, etc. may be stored in an internal database 470 or external database 180 (shown in FIG. 1) in communication with network server 160, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, network server 160 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, network server 160 may include memory 440 that may include one or more programs 442 to perform one or more functions of the disclosed embodiments. Moreover, processor 420 may execute one or more programs located remotely from account information display system 100. For example, network server 160 may access one or more remote programs, that, when executed, perform functions related to disclosed embodiments.

Programs 450 stored in memory 440 and executed by processor(s) 420 may include one or more server app(s) 452 and operating system 454. Server app(s) 452 may incorporate one or more apps configured to receive input of information related to tracking patient statuses such as receiving patient attributes, diagnoses, treatment, and conditions, receiving staff schedules, skills, and performance, receiving one or more hospital rules and legal restrictions, receiving treatment requirements, physicians' orders and regimens associated with patient diagnoses, analyzing received data using one or more rule sets, computer models, or other processing logic, generating data associated with one or more graphical user interfaces, generating one or more communications and/or commands to other computer systems or devices such as user device 120, and updating the graphical user interfaces in real-time based on new data or changes in the analysis results.

In some embodiments, memory 440 may store data 448 including data associated with patients, staff, tasks, assets such as hospital beds (including hospital bed usage), assignment and graphical user interface generation algorithms, historical data, data derived from historical data such as trends, patterns, and correlative relationships. For example, data 448 may include one or more entries including employee data 449 (e.g., identifications of staff, their skill sets, their productivity, their schedules and availability, staff assignment history), patient medical records, patient assignment history, data associated with patient conditions, data associated with patient treatment plans, progression of patient treatment, patient bed assignments, bed availability, bed locations, bed attributes, hospital rules, established hospital procedures, patient itineraries, and legal and restrictions and regulations. Data 448 may also include the current location of the patient, the status of each of the patient physician orders (e.g., lab orders, radiology orders), bed assignment priorities, milestones (e.g., discharge and transfer milestones), transport request status, patient hand-off during shift change, continuity of care data for resource assignments, custom patient attributes, and the real-time statuses of delays or complications in hospital departments and units. In some embodiments, data 448 is stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Network server 160 may communicate with one or more remote memory devices (e.g., third-party server 170 and/or database 180) through network 150 or a different network (not shown). The remote memory devices may be configured to store information and may be accessed and/or managed by network server 160. By way of example only, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database. It should be noted that facility server 130 and/or 3$^{rd}$ party server 170 may include, but are not limited to, all the components and functionality of network server 160. Even though some examples may be described in relation to a particular server, database, terminal, device, etc., any computing device may carry out any of the operations described herein, consistent with the disclosed embodiments.

Figure 5:
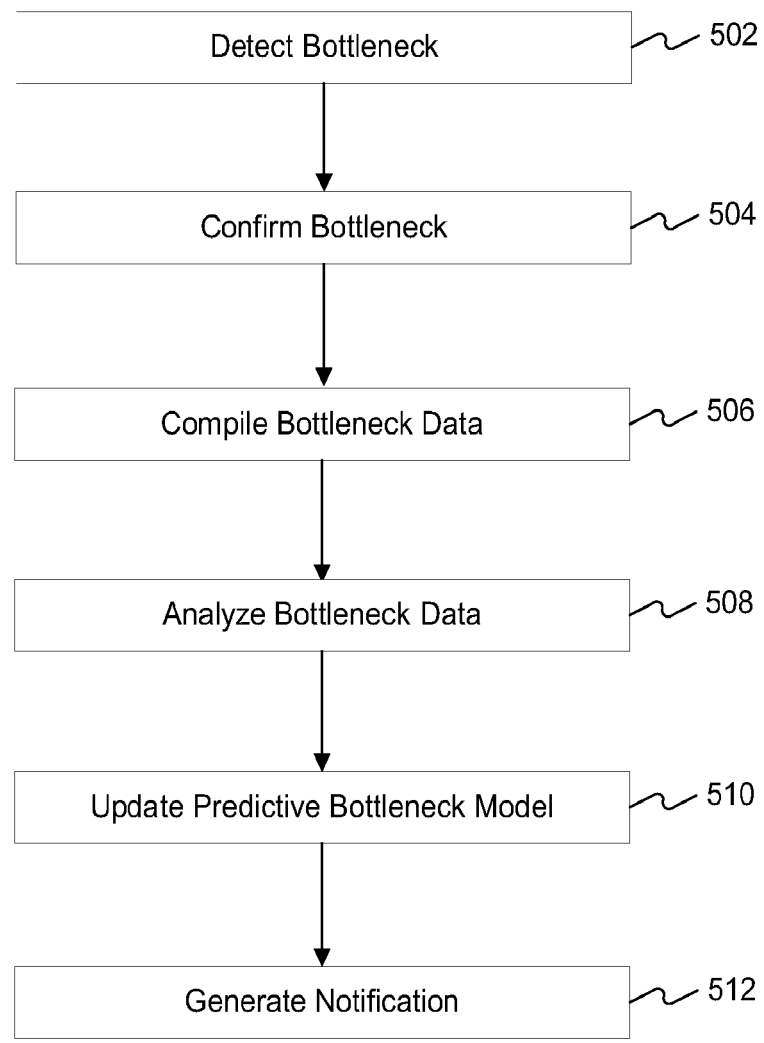
FIG. 5 depicts an example of a flowchart for building predictive bottleneck models.

FIG. 5 illustrates exemplary flowchart for managing bottleneck models. At step 502, process 500 may begin by detecting a bottleneck using techniques disclosed herein. In some embodiments, a bottleneck may be an area of patient care throughput (e.g. a surgery department) that is experiencing an elevated level of delay (e.g., delayed task completion, buildup of a patient queue, etc.). In some embodiments, a bottleneck may be an area of patient care throughput that has a level of throughput that is below a threshold level, or that has a patient queue that is above a threshold level.

A bottleneck may be detected by facility server 130, network server 160, or 3$^{rd}$ party server 170 (i.e., automatically). In other embodiments, a user 125 may detect the bottleneck and enter an indication of the bottleneck (e.g., information detailing the enterprise, facility, area within the facility, timing information, statistics, and/or severity of the bottleneck) at user device 120.

A bottleneck may be detected based on information received at a number of devices. For example, sensing devices 147 may detect particular actions related to a patient (e.g., movement of a patient from one location to another). User device 120 may also receive inputs from a user 125 related to patient care (an entry that a patient has entered surgery, is waiting on a particular department or physician, etc.). Any or all of this information may be sent to another device (e.g. facility server 130), which may examine the information and detect a bottleneck. In some embodiments, a bottleneck may be detected solely based on user input (e.g., user input at a device containing information of a current or hypothetical bottleneck), which may be done to build and/or train a predictive bottleneck model.

At step 504, process 500 may include one or more operations to confirm the bottleneck. For example, after detecting a bottleneck at step 502, facility server 130 may send a prompt to computer terminal 140, user device 120, or another device in computer system 100. In some embodiments, this prompt may include information related to the detected bottleneck and may ask a user 125 to input additional information and/or confirmation of the bottleneck (e.g. by selecting a button as part of a bottleneck confirmation GUI on a display 310). In some embodiments, process 500 may automatically confirm the bottleneck, such as by comparing it to a previously confirmed bottleneck and determining that the two have a threshold degree of similarity. Process 500 may also poll devices, such as sensing devices 147, to gather data relevant to confirming the bottleneck (e.g., patient location data). In some embodiments, process 500 may not carry out another step (e.g., step 510) unless it confirms the bottleneck.

At step 506, process 500 may compile bottleneck data. Bottleneck data may comprise a variety of data from the past (i.e. historical data), including data related to previous bottlenecks at any number of facilities (which may be in the same or different enterprises), facility patient care throughput, enterprise throughput, sensor readings, weather, local news, traffic, natural disasters, emergency transportation, staff schedules, patient itineraries, patient acuity, and the like. Bottleneck data may also include any of these types of data collected at the present time (i.e., real time data). In some embodiments, historical data may have a least one similarity to data related to the detected bottleneck (e.g., real time data). For example, the historical data may be related to the same facility to which the detected bottleneck pertains. As another example, when current weather data (i.e., real time weather data at the time the bottleneck is detected) indicates that local weather for the geographical location of a particular facility includes precipitation, the historical data may be related to data gathered from the facility on a day where the weather also included precipitation. In some embodiments, data may be gathered from a web crawler (e.g., local news data collected by a web crawler operated by facility server 130, network server 160, or $3^{rd}$ party server 170). The bottleneck data may be dispersed across a number of sources, source as facility server 130, network server 160, $3^{rd}$ party server 170, and/or database 180. In some embodiments, data related to a previous bottleneck (e.g., data compiled in response to a previously detected bottleneck) may be stored at facility server 130 or network server 160. Data not necessarily related to a previous bottleneck (e.g., weather data) may be stored at a $3^{rd}$ party server 170. Collecting various data from different sources may allow process 500 to provide a more robust and accurate analysis in other steps (e.g., such as correlating certain conditions with a bottleneck in a particular area at step 510). Bottleneck data generated by and/or sourced from sources outside a facility to which the bottleneck pertains may be termed contextual data.

In some embodiments, the bottleneck data comprises data collected over a predetermined time period (e.g., within a threshold number of days prior to the detected bottleneck). In this way, stale data (e.g., data that is outside a range of the predetermined time period) may be eliminated from use in process 500. In some embodiments, the bottleneck data may be based upon particular parameters defined within a model for managing bottlenecks (e.g., a model maintained by network server 160). For example, a model may contain a parameter for a number of hospital admittances per hour, but may not have a parameter for hourly weather, such that applicable historical data may comprise data related to hospital admittances, but not data related to hourly weather.

In some embodiments, bottleneck data may comprise synthetic data. Synthetic data may data received from a user, including subjective data, rather than objective data collected by one or more sensors or other equipment for observing a condition changing in an environment. The synthetic data may incorrectly indicate conditions are not currently present (e.g., heavy traffic conditions when traffic is currently light). In this manner, synthetic data may be used to train and improve a predictive bottleneck model based on possible future situations (such as the predictive bottleneck model updated at step 510).

At step 508, process 500 may analyze the bottleneck data. In some embodiments, this analysis may be performed by network server 160 or $3^{rd}$ party server 170 (i.e., remotely from facility system 102). In other embodiments, such an analysis may be performed by one or more processors within facility system 102 (e.g., at facility server 130).

In some embodiments, analyzing the bottleneck data may involve determining factors that influence the formation and/or severity of a bottleneck, and may involve determining how those factors influence the formation and/or severity of a bottleneck. For example, analyzing the bottleneck data may comprise identifying a statistical correlation between the prevalence of a data element and the formation and/or severity of a bottleneck. As an example, process 500 may identify a statistically recurring prevalence of (i) a data element comprising a local news story containing information of a sports event on a given day and (ii) a bottleneck resulting from an increased admittance of patients suffering from heat stroke on the same day. Based on this recurring prevalence, process 500 may determine that the occurrence of a local sports event increases the chances of a bottleneck at a facility (e.g., a bottleneck at a hospital caused by a surge in admissions of patients needing treatment for heat stroke). In some embodiments, analyzing the bottleneck data may comprise identifying a correlation between a combination of data elements (e.g., a data element comprising a local new story containing information of a sports event on a given day and a data element comprising weather information indicating a heat advisory) and the formation and/or severity of a bottleneck. In some embodiments, the bottleneck may be analyzed using artificial intelligence and/or machine learning, which may or may not use statistical correlations.

At step 510, process 500 may update a predictive bottleneck model as part of an ongoing model training process. In some embodiments, a predictive bottleneck model may be a computer model configured to predict a bottleneck occurring in the future at a facility and/or within an enterprise. The predictive bottleneck model may include a particular rule set, algorithm (e.g., machine learning algorithm), and/or artificial intelligence (AI). In some embodiments, parameters for such a rule set, algorithm, or AI may be contained in a memory component or database of a server (e.g., network server 160). These parameters may be user-configured, machine-configured, or a combination of both. For example, parameters may be added, altered, and/or deleted according to a user input at any device connected to local network 110 and/or network 150. Parameters may also be given relative weights. For example, an electronic record may store a set of predetermined relative weights. Such weights may be determined automatically over time using modeling techniques and rule sets to identify the most influential parameters. In some embodiments, relative weights may be identified by a user through an input to a device. As an example of a relative weight, an electronic record may indicate that parameters associated with data from a facility (e.g., a hospital) are to have a 15% increased influence on the model relative to other parameters.

Updating the predictive bottleneck model may comprise automatically adding, altering, and/or deleting any number of parameters of the model. In some embodiments, recommended changes to the model may be generated (e.g., by a processor 420 running a program 442 at a $3^{rd}$ party server 170) and stored (e.g., at memory 440 of or database 180), and the model itself may not be updated until an approval of the recommended changes is received (e.g., with an approval initiated by a user input at a device such as network server 160 or administration terminal 145). In some embodiments, the updated bottleneck model may be used to detect another bottleneck (e.g., a new iteration of process 500 starting at step 502). Any number of the steps in process 500 may be performed iteratively, which may allow for repeated updates of a predictive bottleneck model, increasing its comprehensiveness, accuracy, and/or responsiveness.

An updated bottleneck model may be stored in one or more networked computer systems such as at facility server 130, network server 160, and/or $3^{rd}$ party server 170. In some embodiments, a copy of the model may be stored both internally to the facility system 102 (e.g., at facility server 130) and externally to the facility system 102 (e.g., at network server 160). In this way, should the facility system 102 lose connectivity to an external device having the model (e.g., network server 160), it may continue to use the internal copy. In some embodiments, older versions of a model may be stored, and may be used to downgrade a current model and/or used to improve updates for future models. Such older versions may be deleted from time to time based on, for example, age of the version and/or memory space used by the version.

Figure 8:
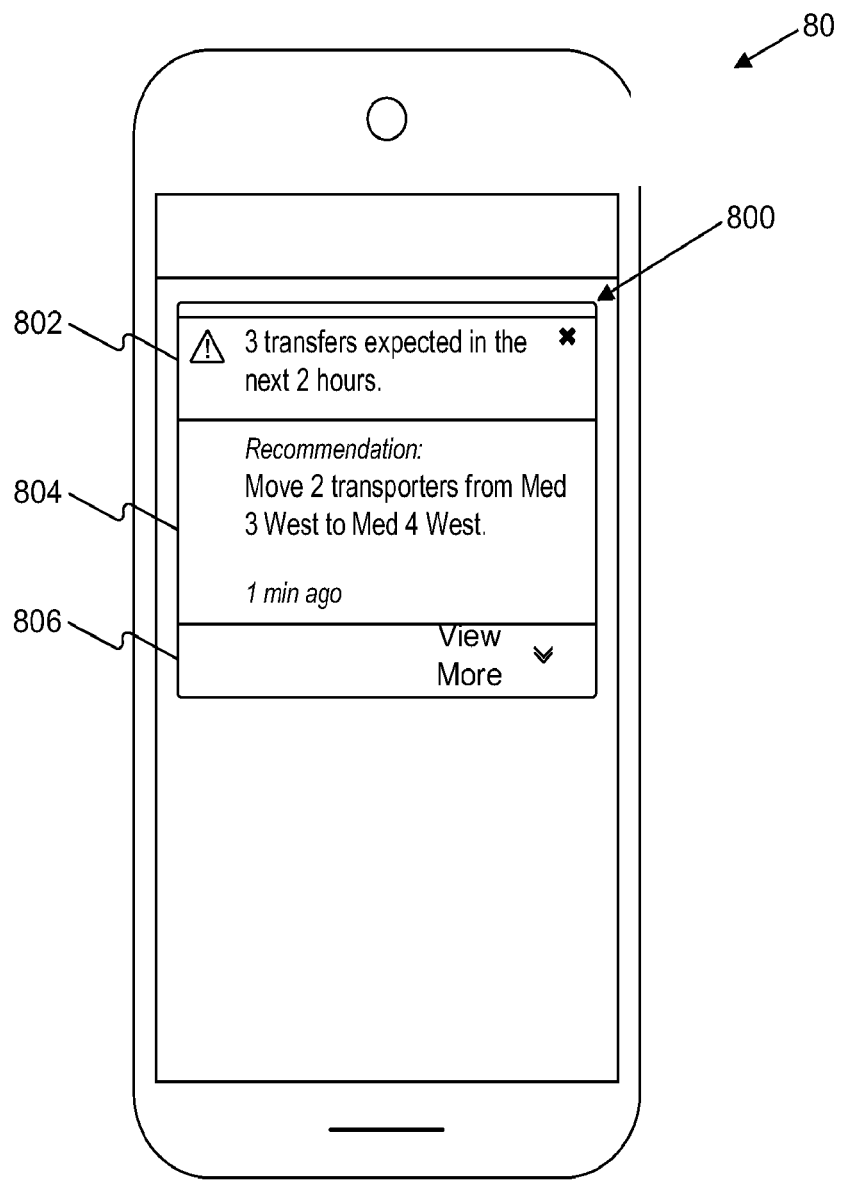
FIG. 8 depicts an example of a bottleneck notification displayed on a mobile phone.

At step 512, process 500 may generate a notification. This notification may be sent to user device 120, administration terminal 145, network server 160, or any other device connected to local network 110 or network 150. This notification may comprise an indication that a model was updated automatically, a model requires user input before it will be updated, and/or a model will not be updated (e.g., due to inconclusive analysis performed at step 508, or due to lack of confirmation of a bottleneck at step 504). In some embodiments, a notification may comprise indications of changes or recommended changes to parameters, the bottleneck data compiled at step 506, a copy of the updated model, and/or other information related to the analysis of the bottleneck data. The notification may also show a likelihood of accuracy of the bottleneck (high confidence of bottleneck, low confidence of bottleneck, 60% confidence, etc.). In instances where user input is received (e.g., at a device to which the notification is sent), a user may modify the bottleneck dataset used to update or suggest an update to a bottleneck model (e.g. indicate that a data source was corrupted and that its past three hours of collected data should be ignored), select parameters of the model to change, select specific changes to the parameters, and/or otherwise coordinate updating the model. In some embodiments, the notification may include a recommendation for how to address the bottleneck. FIG. 8 shows an example of one such notification. Such a recommendation may be generated in a manner similar to that described with respect to step 610, discussed below.

Figure 6:
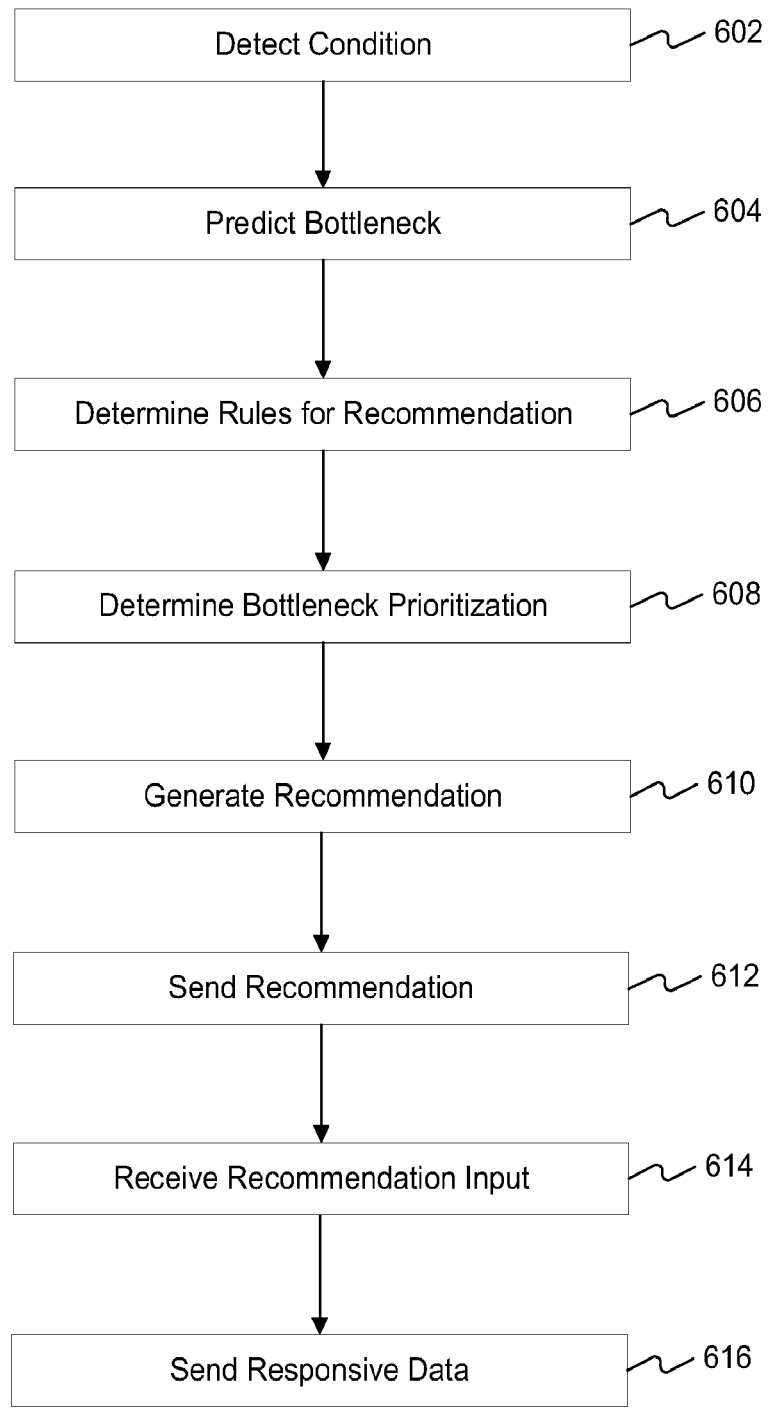
FIG. 6 depicts an example of a flowchart for implementing computer models for predicting bottlenecks.

FIG. 6 is an exemplary flowchart for generating and providing bottleneck recommendations to mitigate a bottleneck. At step 602, process 600 may detect a condition. In some embodiments, this condition may be associated with a bottleneck. The condition may comprise an event (e.g., an admittance of a patient to a hospital) and/or an ongoing state (e.g., ongoing rainy weather throughout a day). In some embodiments, the condition may be represented by a parameter in a predictive bottleneck model, such as the model discussed with respect to process 500. In some embodiments, multiple conditions may be detected, which may or may not have occurred near the same time (e.g., the weather changing to rain and a facility employee missing a shift). A condition may be determined from bottleneck data received at a device performing process 600 (e.g., network server 160 may receive data relating to patient transporter demand from a device within facility system 102). In some embodiments, multiple models may exist (e.g., as part of programs 442 on network server 160), which may be configured to detect different conditions or sets of conditions related to any number of bottlenecks.

At step 604, process 600 may include operations to predict a bottleneck (such as a bottleneck as described with respect to process 500). In some embodiments, process 600 may predict the bottleneck using a predictive bottleneck model (e.g., as discussed with respect to process 500). For example, a predictive bottleneck model may receive a number of parameters from a plurality of sources, and output an indication that a bottleneck is predicted to occur in a future time period based on a combination of conditions (or a single condition) satisfying a number of parameters or rules of the model (e.g., a number of scheduled discharges reaching a certain threshold defined by the parameter). Process 600 may predict any number of bottlenecks, which may be based on different bottleneck models, different parameters, different conditions, etc.

At step 606, process 600 may determine rules according to which a recommendation may be generated. These rules may be part of a predictive bottleneck model, part of a separate model (i.e. a recommendation model), and/or may be part of a rule table, any of which may be stored in a device in computer system 100, consistent with the disclosed embodiments. In some embodiments, the determined rules may take the form of a weighted decision tree. The determined rules may have been originally generated according to any degree of user input and machine learning.

The rules may be determined based on the entity for which recommendations will be generated (i.e., at step 610). For example, an enterprise, which may be larger than a facility and/or have different stakeholders and desired outcomes, may have different rules for addressing bottlenecks.

At step 608, process 600 may determine a bottleneck prioritization. For example, if multiple bottlenecks are predicted at step 604, or if a bottleneck is predicted while a current bottleneck is ongoing (i.e., detected such as according to process 500), process 600 may determine that one bottleneck (whether predicted or current) is of a higher priority than another bottleneck. In some embodiments, this prioritization is determined based on a model, rule table, and/or weighted decision tree. In other embodiments, the prioritization may be determined based on an outcome that results in the lowest overall amount of bottleneck across a facility or enterprise. For example, a device performing process 600 may simulate addressing a set of bottlenecks in different orders and/or with different corrective actions, and determine that an order (i.e., prioritization) and/or set of corrective actions results in the fastest overall patient flow within a hospital. In some embodiments, the prioritization may be partially or entirely based on user-chosen prioritization of bottlenecks (e.g., a user 125 may give input at user device 120 that instructs network server 160 to use a particular bottleneck configuration).

At step 610, process 600 may generate a recommendation. In some embodiments, the recommendation may be generated using a recommendation model. For example, a network server 160 may have a recommendation model to which it applies bottleneck data received from facility server 130.

The recommendation may be generated according to the rules determined at step 606 and/or the bottleneck prioritization determined at step 608. For example, the recommendation may be tailored by applying the rules and prioritization to a bottleneck (or multiple bottlenecks) while taking into account a set of bottleneck data. For example, process 600 may take into account an element of bottleneck data indicating that a surge in patient discharges is expected in the near future (e.g., based on scheduling data), and may recommend expediting current patient discharges to free up resources prior to the surge in response. As another example, process 600 may take into account that transporter demand is low in a first part of a hospital and is elevated in a second part of a hospital, and may recommend shifting staff from the first part to the second part.

Figure 9:
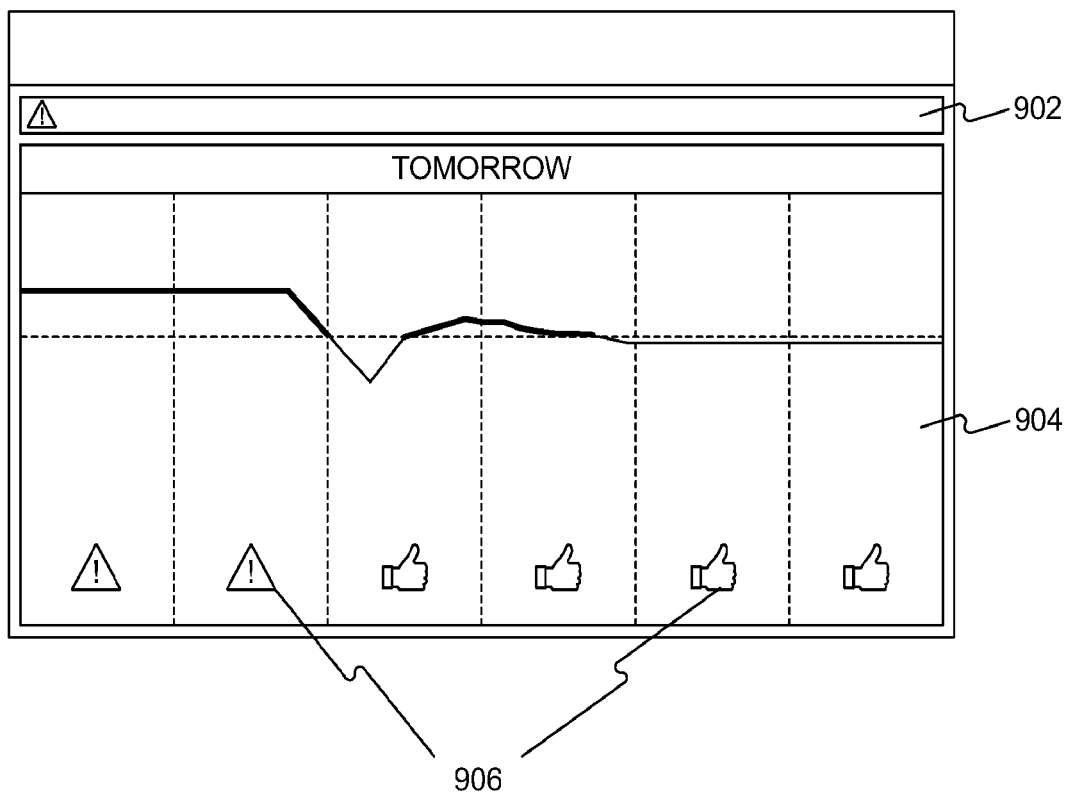
FIG. 9 depicts a predicted bottleneck graphical user interface (GUI).
Figure 10:
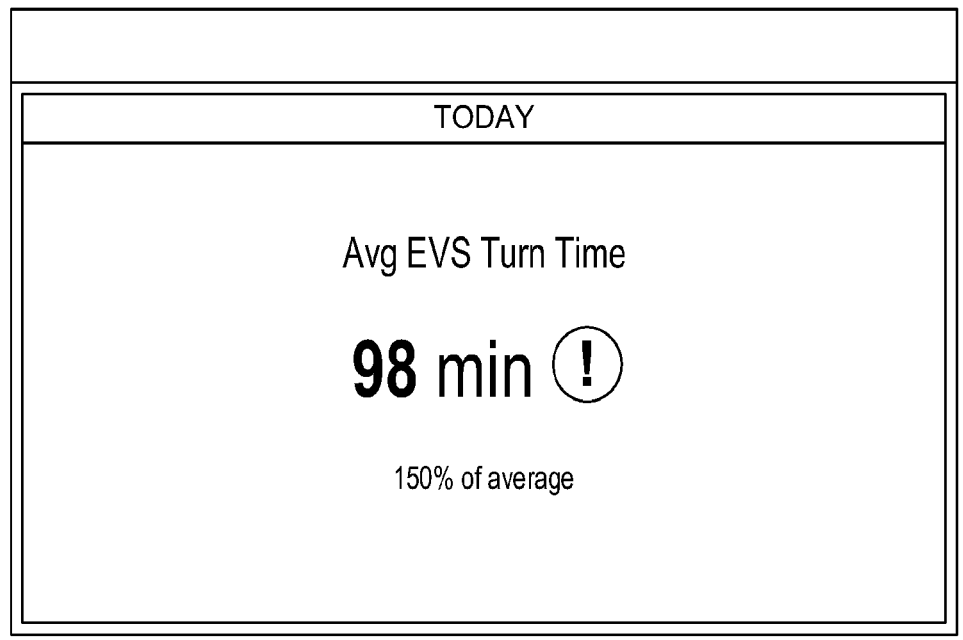
FIG. 10 depicts a current bottleneck graphical user interface (GUI).
Figure 10:
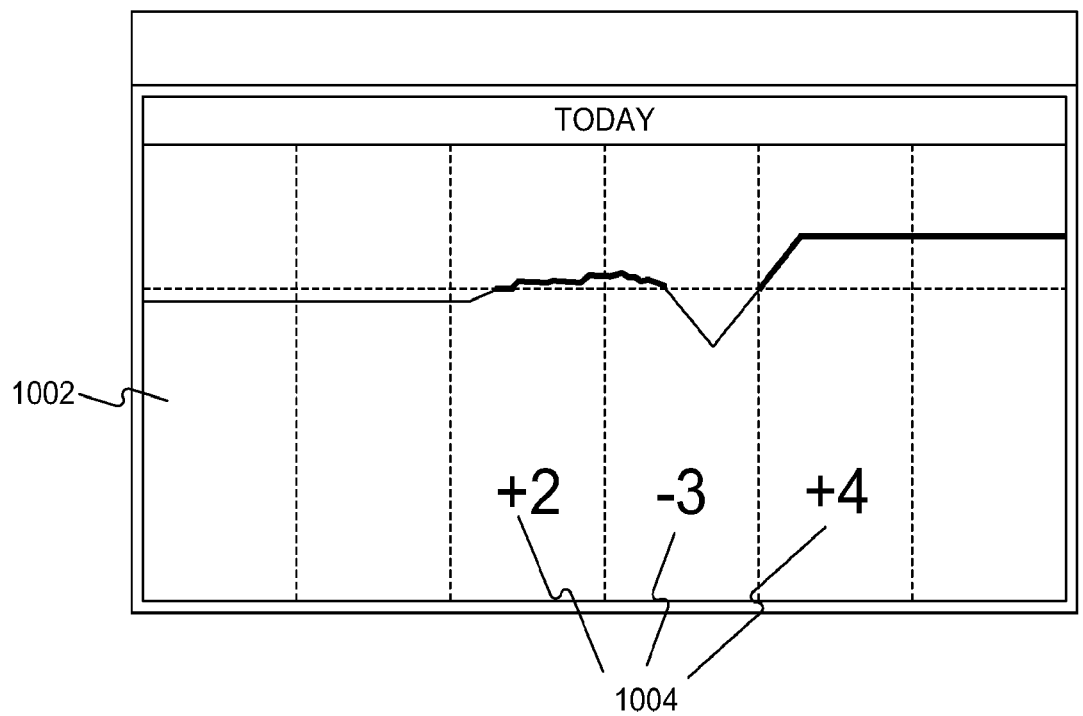

At step 612, process 600 may send a recommendation to a particular destination, such as user device 120, administration terminal 145, computer terminal 140, or any other computing device. Once sent, a user may view (e.g., at display 210 or 310) information related to the predicted bottleneck and the recommendations generated based on the predicted bottleneck. This information may include text, graphics, charts, graphs, maps (e.g., a heatmap showing a degree of patient flow within different areas of a hospital), animations, or any other element capable of display and suitable for informing a user about a predicted bottleneck and/or related recommendations. FIGS. 8, 9, and 10 contain examples of such displayed information.

In some embodiments, the recommendation may also be tailored based on such a destination. For example, a recommendation generated for an administrator using administration terminal 145 may include may high-level statistical information about patient flow, whereas a recommendation generated for a user 125 (e.g., a transporter), may only include information related to how the user's role in a facility may impact a predicted bottleneck.

At step 614, process 600 may receive recommendation input. In some embodiments, this recommendation input may be initially input at a device (e.g., user device 120, administration terminal 145, computer terminal 140, etc.). For example, after the recommendation is received at its destination, a user viewing the recommendation at a computer terminal 140 may select a corrective action (e.g., using a keyboard and mouse connected to I/O 230), which may be a corrective action recommended by a device carrying out process 600. In some embodiments, a user may select a corrective action from among a list of multiple possible corrective actions and/or a list of multiple recommended corrective actions. A corrective action may comprise any number of binary choices (i.e., expedite a discharge for a patient or not) and/or spectrums of choices (i.e., move 0-5 transporters from one wing to another).

At step 616, process 600 may send responsive data to other devices, which may be based on the recommendation input received at step 614. For example, if a corrective action of "expedite discharge of patient John Doe" is received based on a user selection at computer terminal 140, the receiving device may (i) send a notification to a user device 120 or computer terminal 140 associated with a caretaker of John Doe, where the notification indicates that patient John Doe's discharge should be expedited, and/or (ii) alter a patient schedule associated with John Doe stored in facility server 130. As another example, if a corrective action of "transfer transporter Jane Smith to Wing Z" is selected at computer terminal 140, the receiving device may send a notification to a user device 120 associated with Jane Smith indicating that work assignments have been altered, and/or may alter a work schedule associated with Jane Smith stored in facility server 130 and/or user device 120. These are merely examples and not meant to limit the disclosure, as other responsive actions are of course possible and fully within the scope of this disclosure.

Figure 7:
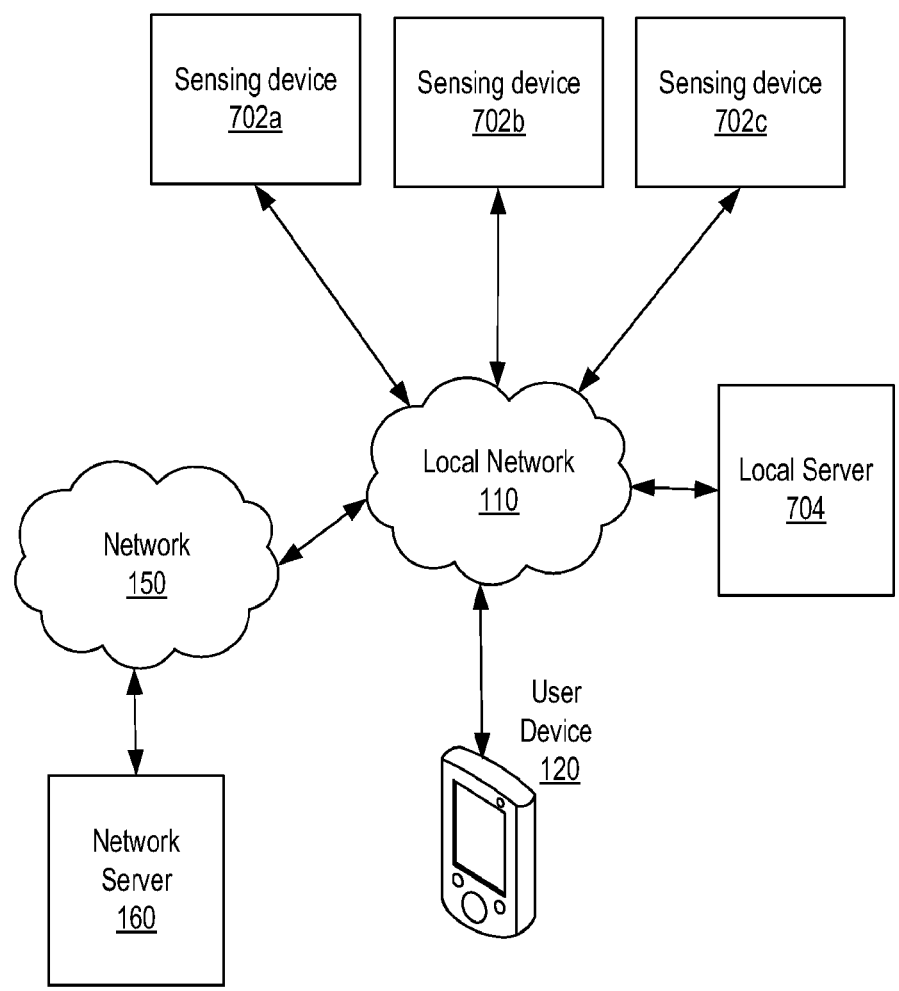
FIG. 7 depicts an exemplary system for managing resource bottlenecks detected within a sensor network.

FIG. 7 illustrates sensor network environment 700, which is an exemplary instance of computer system 100, and which may implement either or both of processes 500 and 600. Sensor network environment 700, being merely exemplary, in no way limits the scope of possible embodiments encompassed by the present disclosure.

Sensor network environment 700 may include a local network 110 that is connected to a number of sensing devices 702a, 702b, and 702c. Sensing devices 702a, 702b, and 702c may be instances of a sensing device 147, as discussed with respect to FIG. 1. In some embodiments, sensing devices 702a, 702b, and 702c may monitor for an action indicative of usage of a resource relative to the usage capacity of that resource. For example, sensing devices 702a, 702b, and 702c may monitor a location of a doctor within a hospital and determine that the doctor is within an operating room and is therefore, as a resource, being fully used. As another example, a virtual sensing devices 702a may determine that a networked device, such as a printer, currently has several tasks queued, and therefore currently has a high resource usage level. Sensor network environment 700 also includes local network 110, user device 120, network 150, and network server 160, all of which are described with respect to FIG. 1. Though not shown, user device 120 may also connect directly to network 150, either in addition to, or instead of, connecting directly to local network 110. Sensor network environment 700 also include local server 704, which is connected to local network 110. Local server 704 may be an instance of administration terminal 145, facility server 130, computer terminal 140, a special purpose server, and/or any computing device.

Either or both of processes 500 and 600 may be implemented on sensor network environment 700. In some embodiments, a sensor network environment 700 implementing process 500 may only implement steps 502 and 508, rather than another combination of the steps of process 500. For example, at step 502, sensor network environment 700 may detect a bottleneck based on at least one sensor reading at any number of sensing devices 702a, 702b, and 702c that indicates a high resource usage of a particular resource. These resources may include, but are in no way limited to: hospital staff, medications, scanning equipment, parking spaces, roadway space, bandwidth, processing capacity, storage space for physical objects, data storage space, assembly line equipment, airport terminal space, and/or any usable resource with a finite usage capacity. After the sensor reading is detected, bottleneck data may be routed from a sensing device to local network 110, where it may be sent to local server 704, user device 120, and/or network server 160 for analysis (e.g., performance of step 508). After the bottleneck data is analyzed, resource usage may be automatically adjusted in response. As one example, if an internal medicine unit is bottlenecked due to unusually high usage of a particular drug, requests for that drug may be temporarily delayed to mitigate the bottleneck. Resource usage may also be shifted, for example patients may be moved from a resource-strained wing of a hospital to a less-resource-strained wing of the hospital. As another non-limiting example, if a driving lane on a highway is blocked due to an accident or debris, traffic may be automatically rerouted to other lanes of the highway (e.g., by illuminating signs over usable lanes with arrows and illuminating signs over unusable lanes with an "X").

In some embodiments, after the bottleneck data is analyzed, sensor network environment 700 may implement process 600, such as to predict and prevent future bottlenecks. For example, a predictive bottleneck model may appreciate that patient visitations are elevated on Saturdays and Sundays, and may automatically, or with user input, staff additional personnel to check in hospital visitors. As another non-limiting example, a predictive bottleneck model may understand that a currently high level of occupancy in an office building may cause a bottleneck of queries to a database used by employees in the building. In response, requests to the database may be intentionally delayed to temporally stretch the usage of the database.

FIG. 8 shows an illustration of an example of a bottleneck notification displayed on a mobile phone 80, which may be a user device 120. In this example, a bottleneck notification 800 is displayed on the device (e.g., as part of process 500 and/or 600). Of course, bottleneck notification 800 may be displayed on any number of devices suitable for display, such as administration terminal 145, computer terminal 140, and/or network server 160. Bottleneck notification 800 may include any number of areas, and in this example includes bottleneck description area 802, recommendation area 804, and information button 806. Bottleneck notification 800 may help facilitate process 500 and/or 600, consistent with the disclosed embodiments.

Bottleneck description area 802 may describe varies aspects of a bottleneck that has been detected (e.g., according to process 500) and/or predicted (e.g., according to process 600). For example, bottleneck description area 802 may describe a type of bottleneck (e.g. an elevated number of transfers) and/or a time of the bottleneck (currently happening, predicted in two hours, etc.).

Recommendation area 804 may include information related to addressing a bottleneck, whether the bottleneck is present or is predicted to happen in the future. For example, recommendation area 804 may describe a suggested action that will alleviate the bottleneck (e.g., transfer staff from one area to another).

Information button 806 may be selectable by a user via an input at a device displaying bottleneck notification 800. Upon selection, a new display area may drop down beneath recommendation area 804. In other embodiments, a new GUI may display on user device 120. This new display area or new GUI may include other information related to the bottleneck, such as data sources used to detect and/or predict the bottleneck, entities impacted by the bottleneck (e.g. a patient, a wing of a hospital, a resource within a facility, etc.), a severity of the bottleneck as a whole or relative to a particular entity, parameters of a bottleneck model, and the like. As one of ordinary skill in the art would appreciate, any number of display areas, buttons, toggles, graphs, charts, animations, graphics, sliders, selectables, predicted bottleneck GUIs 900, current bottleneck GUIs 1000A or 1000B, or any other graphical user interface elements may be displayed as part of bottleneck notification 800 and/or in response to a user input.

FIG. 9 shows an illustration of a predicted bottleneck GUI 900. Predicted bottleneck GUI 900 may be displayed on any number of devices suitable for display, such as user device 120, administration terminal 145, computer terminal 140, and/or network server 160. Predicted bottleneck GUI 900 may show information related to a bottleneck predicted to possibly occur in the future. In the example shown, predicted bottleneck GUI 900 includes a chart indicating potential strain on a particular resource in the future (e.g., as indicated by a height of a line on a horizontal axis). Predicted bottleneck GUI 900 may help facilitate process 500 and/or 600, consistent with the disclosed embodiments.

Predicted bottleneck GUI 900 may include a warning notification area 902. Warning notification area 902 may include pertinent information to the predicted bottleneck, such a severity of the bottleneck, type of bottleneck, or other such relevant information related to a bottleneck, consistent with the disclosed embodiments.

The chart within predicted bottleneck GUI 900 may be divided into any number of time periods 904. Each time period 904 may have a degree of resource strain (e.g., a number of expected discharges) associated with it, which may be determined by an algorithm that determines the integral of the line graph for that time period 904, or other way of calculating the usage of the resource in view of a capacity. In some embodiments, a user may select a time period 904, which may cause further information about that time period 904 to be displayed.

Predicted bottleneck GUI 900 may also include severity indicators 906. In some embodiments, predicted bottleneck GUI 900 may only display one severity indicator 906. In other embodiments, predicted bottleneck GUI 900 may display multiple severity indicators 906, such as one for each time period 904 (i.e., as shown in FIG. 9). A severity indicator 906 may indicate a severity (e.g. critical severity) and/or likelihood of a bottleneck (e.g., 75% likelihood of occurrence), which may be associated with a specific time period 904. In some embodiments, a severity indicator 906 may be based on whether a predicted future resource usage (e.g., a number of occupied beds in a hospital) has reached a certain threshold. A severity indicator 906 may be displayed with a time period 904 with which it is associated. In some embodiments, a severity indicator 906 may change dynamically as bottleneck data changes. For example, if an absent employee reports to work, the strain on a receiving department may decrease such that its resource usage falls below a particular threshold. As one of ordinary skill in the art would appreciate, any number of display areas, buttons, toggles, graphs, charts, animations, graphics, sliders, selectables, bottleneck notifications 800, current bottleneck GUIs 1000A or 1000B, or any other graphical user interface elements may be displayed as part of predicted bottleneck GUI 900 and/or in response to a user input.

FIG. 10 shows exemplary illustrations of current bottleneck GUI 1000A and current bottleneck GUI 1000B. Current bottleneck GUI 1000A and/or 10006 may be displayed on any number of devices suitable for display, such as user device 120, administration terminal 145, computer terminal 140, and/or network server 160. Current bottleneck GUI 1000A and/or 10006 may help facilitate process 500 and/or 600, consistent with the disclosed embodiments.

Current bottleneck GUI 1000A may display information related to a current bottleneck. For example, current bottleneck GUI 1000A may display a current throughput time, a current resource usage, or the like. In some embodiments, current bottleneck GUI 1000A may display a statistic related to the current bottleneck (as shown, for example, in FIG. 10, "150% of average"). Current bottleneck GUI 1000A may include data generated from the beginning of a day until the present, data generated during the past hour until the present, or any other set of data substantially generated in real time.

Current bottleneck GUI 1000B may display information related to current and/or recent resource usage. For example, current bottleneck GUI 1000B may display a chart indicating strain on a particular resource throughout a period of time, such as a number of hospital beds.

The chart within current bottleneck GUI 1000B may be divided into any number of time periods 1002. Each time period 1002 may have a degree of resource strain (e.g., a number of hospital beds occupied) associated with it, which may be determined by an algorithm that determines that integral of the line graph for that time period 904. In some embodiments, a user may select a time period 1002, which may cause further information about that time period 1002 to be displayed.

Current bottleneck GUI 1000B may also include any number of change indicators 1004. In some embodiments, current bottleneck GUI 1000B may display one change indicator 1004 for each time period 1002 (i.e., as shown in FIG. 10). A change indicator 1004 may indicate a change in the amount of a particular resource used at a facility and/or within an enterprise. A change indicator 1004 may be displayed with a time period 1002 with which it is associated. In addition to or instead of a change indicator 1004, current bottleneck GUI 1000B may display severity indicators, such as those described with respect to FIG. 9. As one of ordinary skill in the art would appreciate, any number of display areas, buttons, toggles, graphs, charts, animations, graphics, sliders, selectables, bottleneck notifications 800, predicted bottleneck GUIs 1000A or 1000B, or any other graphical user interface elements may be displayed as part of predicted bottleneck GUI 900 and/or in response to a user input.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

The invention claimed is:

1. A computerized system for managing predictive bottleneck models, the system comprising:
   at least one processor in communication with a communications network; and
   a storage medium comprising instructions that when executed, configure the at least one processor to:
   create a predictive bottleneck model, wherein the predictive bottleneck model is a machine-learning model that predicts future bottleneck and generates interactive graphical user interfaces having recommendations based upon an analysis of data, wherein to create the predictive bottleneck model comprises steps of:
   receiving, at a facility system and from a user device and sensing devices that are located throughout a facility and that monitor one or more conditions of the facility and capture tracking data of a patient throughout the facility, bottleneck data indicating a bottleneck within the facility based upon movement of the patient within the facility as identified from the captured tracking data;
   confirming, from data gathered from polling the sensing devices, the bottleneck;
   compiling, based on the received indication, contextual data associated with the bottleneck, wherein the contextual data comprises historical data and real time data generated and sourced from sources outside the facility and identifying conditions corresponding to historical bottlenecks and the bottleneck and having at least one similarity to data related to the bottleneck;
   analyzing the bottleneck data and the contextual data conjunctively, wherein the analyzing comprises determining factors that influence the formation and severity of a bottleneck;
   determining a relationship between the bottleneck data and the contextual data, wherein the determining comprises identifying a statistical correlation between the prevalence of a data element and the formation and severity of a bottleneck; and
   adding the relationship to a bottleneck dataset, wherein the bottleneck dataset comprises a training dataset for the predictive bottleneck model;
   train the predictive bottleneck model using the bottleneck dataset;
   in response to a user input via the interactive graphical user interface containing information related to a possible bottleneck within the facility, predict, by the predictive bottleneck model, bottlenecks occurring at a future time within the facility, and recommend, by the predictive bottleneck model, at least one corrective action to mitigate the bottlenecks occurring at a future time within the facility;
   modify the bottleneck dataset utilizing new bottleneck data, contextual data associated with the new bottleneck data, and determined relationship between the new bottleneck data and contextual data associated with the new bottleneck data; and update the predictive bottleneck model using the modified bottleneck dataset and using the updated predictive bottleneck model to make further predictions regarding bottlenecks occurring at a new future time within the facility.

2. The computerized system of claim 1, wherein the instructions further configure the at least one processor to provide at least one fix to mitigate the bottleneck within the facility.

3. The computerized system of claim 1, wherein the bottleneck data comprises tracking data from sensors indicating movements of patients within the facility.

4. The computerized system of claim 1, wherein the bottleneck data comprises data indicating an area within the facility is experiencing at least one of: a level of throughput below a predetermined threshold level, a patient query above a threshold level, and an elevated level of delay.

5. The computerized system of claim 1, wherein the instructions further configure the at least one processor to confirm the bottleneck by comparing the bottleneck data to a previously confirmed bottleneck.

6. The computerized system of claim 1, wherein to compile comprises compiling historical data related to previous bottlenecks.

7. The computerized system of claim 1, wherein to analyze comprises determining factors that influence a severity of the bottleneck and determining how the factors influence the severity.

8. The computerized system of claim 1, wherein to determine comprises identifying a statistically recurring prevalence of the bottleneck and at least a portion of the contextual data.

9. The computerized system of claim 1, wherein the predictive model comprises parameters that comprise weights determined utilizing modeling techniques.

10. The computerized system of claim 1, wherein to update comprises automatically modifying parameters of the predictive model based upon the relationships.

11. A computerized method for managing predictive bottleneck models, the method comprising:

creating, by at least one processor, a predictive bottleneck model, wherein the predictive bottleneck model is a machine-learning model that predicts future bottlenecks and generates interactive graphical user interfaces having recommendations based upon an analysis of data, wherein the creating the predictive bottleneck model comprises steps of:

receiving, at a facility system and from a user device and sensing devices that are located throughout a facility and that monitor one or more conditions of the facility and capture tracking data of a patient throughout the facility, bottleneck data indicating a bottleneck within the facility based upon movement of the patient within the facility as identified from the captured tracking data;

confirming, from data gathered from polling the sensing devices, the bottleneck;

compiling, based on the received indication, contextual data associated with the bottleneck, wherein the contextual data comprises historical data and real time data generated and sourced from sources outside the facility and identifying conditions corresponding to historical bottlenecks and the bottleneck and having at least one similarity to data related to the bottleneck;

analyzing the bottleneck data and the contextual data conjunctively, wherein the analyzing comprises determining factors that influence the formation and severity of a bottleneck;

determining a relationship between the bottleneck data and the contextual data, wherein the determining comprises identifying a statistical correlation between the prevalence of a data element and the formation and severity of a bottleneck;

adding the relationship to a bottleneck dataset, wherein the bottleneck dataset comprises a training dataset for the predictive bottleneck model;

training the predictive bottleneck model using the bottleneck dataset;

in response to a user input via the interactive graphical user interface containing information related to a possible bottleneck within the facility, predicting, by the predictive bottleneck model, bottlenecks occurring at a future time within the facility, and recommending at least one corrective action to mitigate the bottlenecks occurring at a future time within the facility;

modifying the bottleneck dataset utilizing new bottleneck data, contextual data associated with the new bottleneck data, and determined relationship between the new bottleneck data and contextual data associated with the new bottleneck data; and updating the predictive bottleneck model using the modified bottleneck dataset and using the updated predictive bottleneck model to make further predictions regarding bottlenecks occurring at a new future time within the facility.

12. The computerized method of claim 11, further comprising providing at least one fix to mitigate the bottleneck within the facility.

13. The computerized method of claim 11, wherein the bottleneck data comprises tracking data from sensors indicating movements of patients within the facility.

14. The computerized method of claim 11, wherein the bottleneck data comprises data indicating an area within the facility is experiencing at least one of: a level of throughput below a predetermined threshold level, a patient query above a threshold level, and an elevated level of delay.

15. The computerized method of claim 11, further comprising confirming the bottleneck by comparing the bottleneck data to a previously confirmed bottleneck.

16. The computerized method of claim 11, wherein the compiling comprises compiling historical data related to previous bottlenecks.

17. The computerized method of claim 11, wherein the analyzing comprises determining factors that influence a severity of the bottleneck and determining how the factors influence the severity.

18. The computerized method of claim 11, wherein the determining comprises identifying a statistically recurring prevalence of the bottleneck and at least a portion of the contextual data.

19. The computerized method of claim 11, wherein the updating comprises automatically modifying parameters of the predictive model based upon the relationships.

20. A non-transitory computer readable medium storing instructions which, when executed, cause at least one processor to perform operations for managing predictive bottleneck models, the operations comprising:

creating a predictive bottleneck model, wherein the predictive bottleneck model is a machine-learning model that predicts future bottlenecks and generates interactive graphical user interfaces having recommendations based upon an analysis of data, wherein the creating the predictive bottleneck model comprises steps of:

receiving, at a facility system and from a user device and sensing devices that are located throughout a facility and that monitor one or more conditions of the facility and capture tracking data of a patient throughout the facility, bottleneck data indicating a bottleneck within the facility based upon movement of the patient within the facility as identified from the captured tracking data;

confirming, from data gathered from polling the sensing devices, the bottleneck;

compiling, based on the received indication, contextual data associated with the bottleneck, wherein the contextual data comprises historical data and real time data generated and sourced from sources outside the facility and identifying conditions corresponding to historical bottlenecks and the bottleneck and having at least one similarity to data related to the bottleneck;

analyzing the bottleneck data and the contextual data conjunctively, wherein the analyzing comprises determining factors that influence the formation and severity of a bottleneck;

determining a relationship between the bottleneck data and the contextual data, wherein the determining comprises identifying a statistical correlation between the prevalence of a data element and the formation and severity of a bottleneck;

adding the relationship to a bottleneck dataset, wherein the bottleneck dataset comprises a training dataset for the predictive bottleneck model;

training the predictive bottleneck model using the bottleneck dataset, in response to a user input via the interactive graphical user interface containing information related to a possible bottleneck within the facility, predicting, by the predictive bottleneck model, bottlenecks occurring at a future time within the facility, and recommending at least one corrective action to mitigate the bottlenecks occurring at a future time within the facility;

modifying the bottleneck dataset utilizing new bottleneck data, contextual data associated with the new bottleneck data, and determined relationship between the new bottleneck data and contextual data associated with the new bottleneck data; and updating the predictive bottleneck model using the modified bottleneck dataset and using the updated predictive bottleneck model to make further predictions regarding bottlenecks occurring at a new future time within the facility.

* * * * *

UNITED STATES PATENT AND TRADEMARK OFFICE
CERTIFICATE OF CORRECTION

| | | |
|---|---|---|
| PATENT NO. | : 12,020,809 B2 | Page 1 of 1 |
| APPLICATION NO. | : 17/769252 | |
| DATED | : June 25, 2024 | |
| INVENTOR(S) | : Anjali Tomer et al. | |

It is certified that error appears in the above-identified patent and that said Letters Patent is hereby corrected as shown below:

On the Title Page

Item (72) In the listing of inventors, an additional inventor is to be added. Thus, the listing of inventors should read:
Anjali Tomer, Pittsburgh, PA (US);
Scott Jubeck, Pittsburgh, PA (US);
Ratna Divya Kanthi Bejjam, Bridgeville, PA (US);
Jaimin Arvindbhai Patel, Monroeville, PA (US).

Signed and Sealed this
Eleventh Day of March, 2025

Coke Morgan Stewart
*Acting Director of the United States Patent and Trademark Office*